United States Patent [19]
Hardt et al.

[11] Patent Number: 5,575,778
[45] Date of Patent: Nov. 19, 1996

[54] BLOOD-TAKING DEVICE

[75] Inventors: Stefan Hardt, Baunatal; Frank Finis, Wolfhagen, both of Germany

[73] Assignee: B. Braun Melsungen AG, Melsungen, Germany

[21] Appl. No.: 310,127

[22] Filed: Sep. 21, 1994

[51] Int. Cl.$^6$ ........................................ A61B 5/00
[52] U.S. Cl. .............................. 604/200; 128/760
[58] Field of Search ............................... 604/48, 51, 89, 604/90, 91, 188, 200, 201; 210/518; 128/760, 763

[56] References Cited

FOREIGN PATENT DOCUMENTS

| | | |
|---|---|---|
| 0056609 | 7/1982 | European Pat. Off. . |
| 0305459 | 3/1989 | European Pat. Off. . |
| 2711336 | 9/1978 | Germany . |
| 2734720 | 2/1979 | Germany . |

*Primary Examiner*—Sam Rimell
*Attorney, Agent, or Firm*—Loeb & Loeb LLP

[57] ABSTRACT

A blood-taking device has a comparatively flexible inner tubule and an outer tubule. There is an annular gap between both tubules. The front end of the inner tubule is provided with an end wall pressing against the annular protrusion of an end wall of the outer tubule. In order to fix the inner and outer tubules with respect to each other, the edge of the inner tubule end wall has a locking profile interlocking with a counter profile of the outer tubule. During centrifugation the inwardly directed protrusion sinks into the soft material of the end wall of the inner tubule. Thus, liquid is prevented from entering the annular gap during centrifugation.

7 Claims, 3 Drawing Sheets

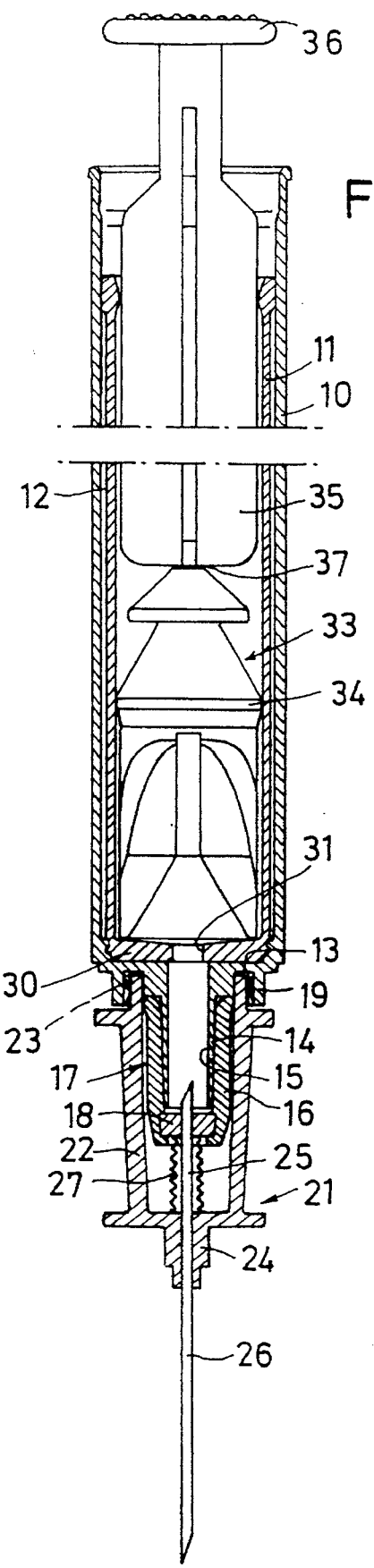
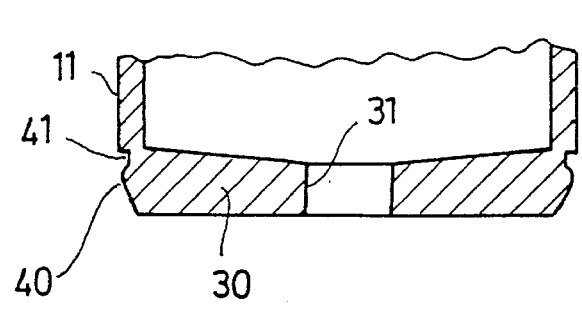
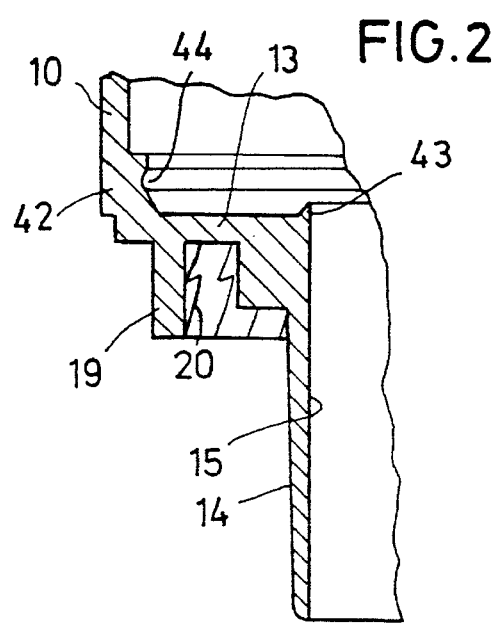

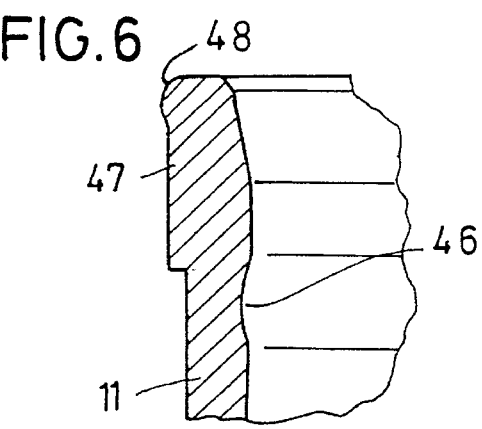
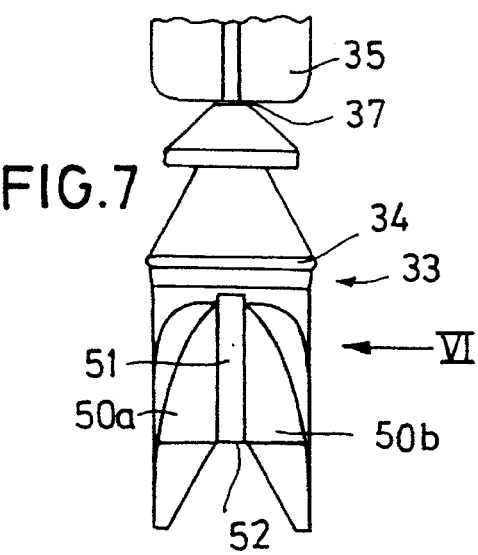
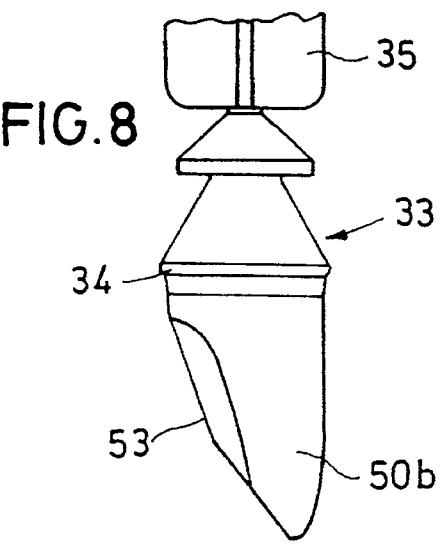
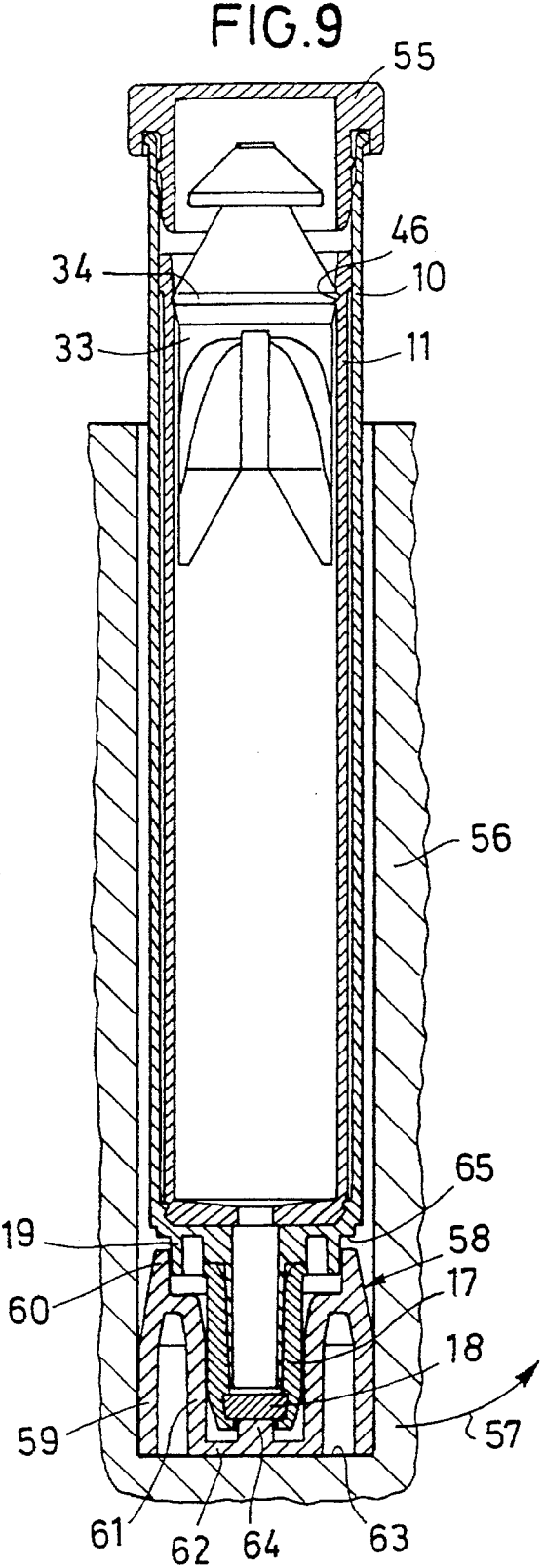

BLOOD-TAKING DEVICE

BACKGROUND OF THE INVENTION

The invention refers to a blood-taking device comprising a tubule in which a separating member is disposed which has a specific gravity that is in between the specific gravities of the blood components to be separated.

Such blood-taking devices are known from German Patents 27 11 336 and 27 34 720, as well as from European Patent 0 056 609. In as far as these blood-taking devices use a tubule of comparatively soft plastics material that, during centrifugation, is expanded by the force of the liquid contained therein and causes a gap to occur around the separating member, the softness of the tubule is often considered disadvantageous. In order to be able to use a soft tubule and yet make the blood-taking device more resistant to exterior influences, European Patent 0 305 459 describes a blood-taking device with a comparatively rigid outer tubule and a comparatively soft inner tubule contained therein which may expand during centrifugation. There is an annular gap between the outer tubule and the inner tubule and the inner tubule contains a separating member provided with a breakable plunger rod so that the separating member can also be used as a plunger for drawing a blood sample into the blood-taking device. In this known blood-taking device, the inner tubule is fixed with respect to the outer tubule either by a stopper that closes both tubules at the same time, or by a press fit engagement extending over a larger portion of the length in the front portion of both tubules, there being no annular gap in this portion because of the press fit. Using an elastomeric stopper for the mutual fixation of the two tubules, a sufficiently firm fit cannot be obtained. It is not possible to achieve a sealing or a sufficient fixation between the soft elastomeric stopper and the soft inner tubule. With the other solution in which there is no annular gap in the front portion and the outer tubule is provided with an inner enlargement in this area, the separating member may get into the portion where no annular gap is provided. In this case, the separating member gets stuck and cannot fulfill its function. It is a further problem that during centrifugation leaks may cause liquid to get past the press fit area into the annular gap. If there is a liquid present in the annular gap, the function of the inner tubule, i.e. the expanding during centrifugation, can no longer be fulfilled.

It is an object of the present invention to provide a blood-taking device comprising an inner tubule and an outer tubule, which is very safe to handle and highly reliable and in which tightness during centrifugation is ensured.

SUMMARY OF THE INVENTION

In the blood-taking device of the present invention the inner and the outer tubule are engaged by interlocking. The interlocking engagement is effected at the location at which the inner tubule is strengthened by the end wall and at which it is highly resistant to compression. The prestressed locking or snap engagement seals the front end of the blood-taking device due to the softness of the material of the inner tubule. Thus, it is ensured that no air is sucked in through the annular gap when the blood-taking device is filled and that no liquid reaches the annular gap between the outer and the inner tubules after the aspiration process. Moreover, the locking engagement prevents inadvertent withdrawal of the inner tubule from the outer tubule, e.g. when aspirating. However, the danger of liquid getting into the annular gap not only prevails during the aspiration process when taking blood, i.e. while blood flows through the cannula hub of the outer tubule into the inner tubule, but above all when centrifugating.

According to a preferred embodiment of the invention, the centrifugal tightness of the outer tubule is guaranteed by the end wall thereof having at least one annular protrusion surrounding the channel of the cannula hub. Due to the locking engagement of the inner and the outer tubules, the end wall of the inner tubule rests prestressed on the annular protrusion and is slightly pressed inward. During centrifugation, this annular protrusion—preferably provided with sharp edges—presses into the bottom of the soft inner tubule, assisted by the pressure exerted by the liquid column in the inner tubule. It ensures the sealing between the inner and the outer tubules both during aspiration and centrifugation, their prime objective, however, being to provide a seal during centrifugation.

If the cannula hub holds a membrane to be pierced by the cannula, there is a danger during centrifugation that the force exerted by the liquid column contained in the inner tubule will cause liquid to escape along the membrane. To prevent this, a centrifuge insert is provided having a receptacle for the cannula insert holding the pierceable membrane, a pin being arranged within the receptacle for supporting the membrane. Thus, the cannula hub with the membrane is sealed particularly well at the puncture site during centrifugation. At the same time, the centrifuge insert supports the outer tubule and prevents the cannula hub from being pressed inward by the centrifugal force. The centrifuge insert may be placed into the centrifuge cup as a separate member, yet it may also be a fixed part of the centrifuge cup. The use of the centrifuge cup with the projection supporting the membrane is of independent importance.

BRIEF DESCRIPTION OF THE DRAWINGS

The following is a detailed description of an embodiment of the present invention in conjunction with the accompanying drawings.

In the figures

FIG. 1 is a longitudinal section of the blood-taking device of the present invention;

FIG. 2 is an enlarged partial longitudinal section of the front end of the outer tubule;

FIG. 3 is a partial longitudinal section of the front end of the inner tubule;

FIG. 6 is a partial longitudinal section of the rear end of the inner tubule;

FIG. 7 is a view of the separating member;

FIG. 8 is a view of the separating member in the direction of the arrow VI—VI of FIG. 7; and FIG. 9 is a longitudinal section of the blood-taking device placed in a centrifuge cup with a centrifuge insert.

DETAILED DESCRIPTION OF A PREFERRED EMBODIMENT

Figure 4:
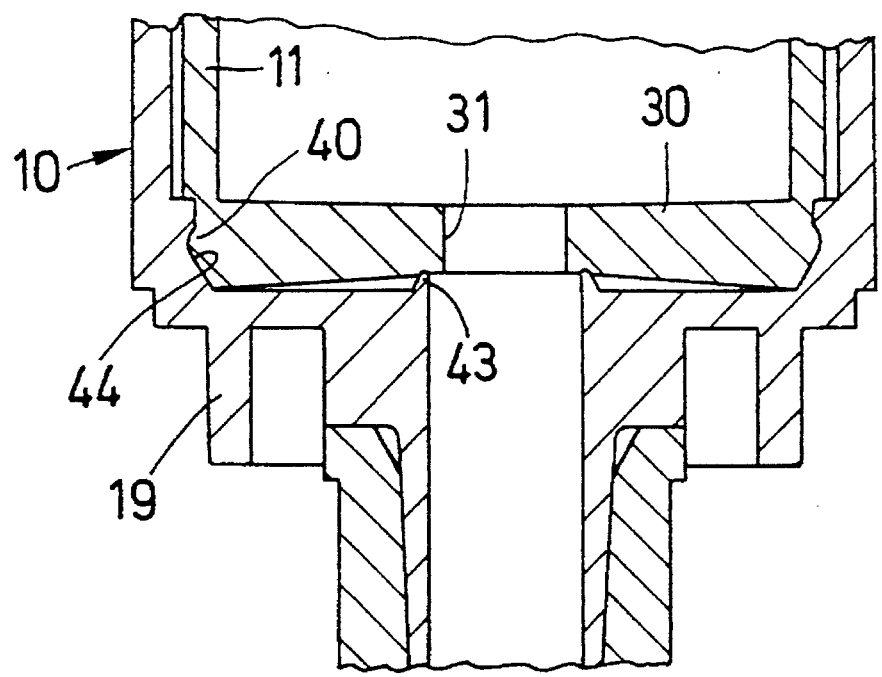
FIG. 4 is a section of the front end of the tubules in the engaged state.

Referring now to FIG. 1, the blood-taking device has a cylindrical outer tubule 10 of comparatively rigid transparent plastics material, in which a transparent cylindrical inner tubule 11 of a material softer than that of the outer tubule 10 is disposed. The inner tubule 11 extends almost over the entire length of the outer tubule 10. There is an annular gap 12 between the outer tubule 10 and the inner tubule 11 that allows for a radial expanding of the inner tubule.

The outer tubule 10 has its front end provided with a front wall 13 formed integrally with the tube wall of the tubule and from which a centrally disposed cannula cone 14 projects. An axial channel 15 extends through the cannula cone 14. A cap 16 forming the cannula hub 17 is plugged onto the cannula cone 14, which cap may be pulled off manually. This cap 16 has a pierceable elastomeric membrane 18 that closes the channel 15.

Furthermore, the front end wall 13 of the outer tubule 10 has a circumferentially extending ring 19 that is open towards the front and is provided with oblique ribs 20 on its interior (FIG. 2). The ring 19 serves as a retaining ring for a multiple sample cannula 21. The multiple sample cannula 21 has a tubular handle member 22 of plastics material that is axially displaceable and rotatable on the substantially cylindrical cannula hub 17 on which it is mounted. The handle member 22 has holding cams 23 which engage between the ribs 20 of the ring 19 and are locked with the ribs 20 by twisting the handle member 22. The front end of the handle member 22 is provided with a hub 24 holding a cannula 26 that is sharpened on both sides and the shorter rear portion 25 of which projects into the handle member 22. The front portion of the cannula projects outward and is for puncturing a vena. The shorter cannula portion 25 is enclosed by a rubber hose 27. When the handle member 22 is set on the cannula hub 17, the rear cannula portion penetrates the protective tube 27 and the membrane 18. In doing so, the protective hose 27 is retained by the front end of the cannula hub 17 and compressed to an accordion-like shape. After having pushed the handle member 22 entirely onto the cannula hub 17, the handle member is locked with the ring 19 in the manner described above and the blood-taking operation may be performed. Instead of using a multiple sample cannula 21, it is possible to set a normal cannula having a receptacle cone at the rear end onto the blood-taking device. To this end, the closing cap 16 is pulled off the cannula cone 14 and the normal cannula is installed.

The front end of the inner tubule 11 has a substantially planar end wall 30 in which a central passage 31 is provided that is in alignment with the channel 15.

The inner tubule includes the separating member 33 with a narrow annular plunger surface 34 which, in the manner of a plunger, divides the volume of the inner tubule into two separate chambers. At the other parts the diameter of the separating member 33 is smaller than that of the plunger surface 34. The rear end of the separating member 33 is connected with a plunger rod 35 consisting of ribs arranged in cross-shape and having a handle plate 36 at the rear end. The plunger rod 35 projects from the open ends of the inner and the outer tubule. If the separating member 33 is in the front end position, i.e. abutting against the end wall 30, the handle plate 36 projects from the outer tubule. By withdrawing the plunger rod 35 and due to the sealing effect of the plunger surface 34, blood is drawn into the inner tubule. After this aspiration, the plunger rod 35 is broken off from the separating member 33 at a rated breaking point 37. Now, the separating member forms a stopper closing the inner tubule.

Referring now to FIG. 3, the edge of the end wall 30 of the inner tubule 11 is formed as a bead-shaped locking profile 40 defined at the rear end by a constriction 41 in the outer surface of the circumferential wall of the inner tubule 11. This locking profile 40 cooperates with a counter profile 44 that is formed on the inside of the outer tubule 10 immediately adjacent its end wall 13 (FIG. 2). The counter profile 44 is an annular depression on the inner side of a strengthened portion 42 that is the transition between the circumferential wall of the outer tubule 10 and the end wall 13. The outer diameter of the locking profile 40 is slightly larger than the inner diameter of the counter profile 44. The locking profile 40 and the counter profile 44 form a pre-stressed snap engagement that locks when the inner tubule is pressed into the outer tubule with force. Due to the elasticity and the softness of the material of the inner tubule 11 the interengaged profiles 40 and 44 have a sealing effect. On the other hand, the rigid counter profile 44 holds the inner tubule 11 with great strength so that the locking engagement is not broken during aspiration, i.e. when withdrawing the plunger rod and the separating member.

The end wall 13 of the outer tubule 10 is provided with an annularly extending pointed protrusion 43 (FIG. 2) that closely surrounds the channel 15 and projects axially into the outer tubule from the end wall 13. When the inner tubule is pressed into the outer tubule with force and the snap engagement catches, the end wall 30 of the inner tubule abuts the protrusion 43 under prestress (FIG. 4). During centrifugation, the protrusion 43 enters the end wall 30. Thus, the junction between the channel 15 and the passage 31 is sealed and liquid is prevented from entering the annular gap 12.

Figure 5:
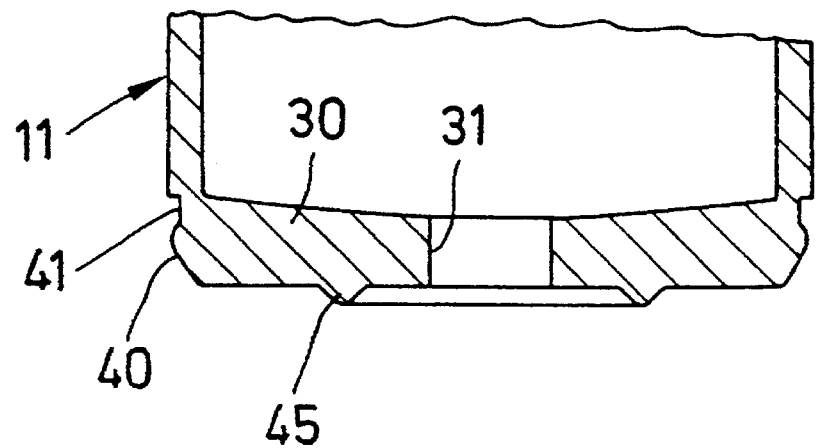
FIG. 5 is a view of a variant with the protrusion at the inner tubule.

The embodiment illustrated in FIG. 5 features an annular protrusion 45 of a preferably triangular cross section that is provided on the outer surface of the end wall 30 of the inner tubule 11. During centrifugation, this protrusion 45 is pressed flat on the end wall 13 of the outer tubule, whereby it provides a seal around the passage 31.

FIG. 6 illustrates the rear end of the inner tubule 11. Here, the inner tubule has an outwardly projecting enlarged portion for frictional support on the outer tubule 10. The inside of the inner tubule 11 is formed with a braking groove 46 that catches the plunger surface 34 of the separating member 33 in the rear end position. In this position, the plunger rod 35 may be broken off from the separating member 33. It is the effect of the braking groove 46 to prevent the withdrawal of the separating member 33. This effect is supported by the enlarged portion 47 that abuts on the outer tubule 10 and prevents an expanding of the inner tubule at the rear end. This prevents the rigid separating member 33 from being inadvertently pulled out of the inner tubule. The braking groove 46 is designed such that it holds the separating member 33 in the rear end position against the action of the vacuum present in the inner tubule. Thus, blood may also be taken by means of the vacuum sampling method according to which a vacuum is generated in the inner tubule 11 immediately before blood is taken. It is a further function of the enlarged portion 47 to seal the annular gap 12 at the rear end. The seal ring 48 prevents serum/plasma supernatant obtained by centrifugation from entering the annular gap 12 when the sample is processed further.

The separating member 33 of FIGS. 6–8 is designed as an asymmetric tilting member according to European Patent 0 056 609 so that, during centrifugation, it can assume different inclined positions with respect to the tubule axis corresponding to the inclination of the centrifuge cup. In front of the plunger surface 34 formed as an annular bead there are two legs 50a, 50b that have ends converging to a tip and are separated by a gap 51. The gap 51 opens to one side and to the front only and is closed at the backside by a circumferential wall 52. The legs 50a and 50b have at least one bevel 53 with respect to the longitudinal axis that allows for inclined positions of the separating member 33 in the expanded inner tubule, The separating member 33 is of a material having a density between those of the blood phases to be separated.

The outer tubule 10 may be closed by setting a closing cap 55 thereon (FIG. 9). The closing cap is seated only in the outer tubule and seals the rear end of the outer tubule. Since this rear end projects beyond the inner tubule, the closing cap will not contact the inner tubule. After the aspiration of blood into the inner tubule, the plunger surface 34 of the separating member 33 is caught in the braking groove 46 to seal the inner tubule at the rear end. The closing cap 55 forms an additional cover. Centrifugation with the closing cap installed is feasible with certain centrifuge designs so as to avoid the aerosol effect.

Referring now to FIG. 9, a centrifuge cup 56 is illustrated being arranged suspended at a radial distance from the centrifuge rotor rotational axis. When the centrifuge rotor rotates, the lower end of the centrifuge cup swings upward in the direction of the arrow 57 so that it eventually takes an almost horizontal position. The bottom of the centrifuge cup 56 is provided with a centrifuge insert 58 of rigid plastics material. The centrifuge insert 58 has a circumferential wall 59 by which it is centered in the centrifuge cup 56. An annular collar 60 protrudes from the circumferential wall 59, which collar surrounds the ring 19 of the outer tubule 10 so as to center the same. The circumferential wall 59 surrounds an annular centering wall 61 that receives the cannula hub 17 in a centering manner. The centering wall 61 is connected with a bottom wall 62 that is supported on the bottom 63 of the centrifuge cup 56. From this bottom wall 62 a centered pin 64 projects which enters the front end of the cannula hub 17 and is supported on the membrane 18. The centrifuge insert 58 is movable within the centrifuge cup and may be removed if need be (e.g. for cleaning).

During centrifugation, the centrifugal force presses the container formed by the outer and the inner tubules against the centrifuge insert 58. The outer tubule 10 rests on the end face of the centering ring 60 by an annular shoulder 65 surrounding the ring 19. At the same time, the pin 64 is pressed into the rubber membrane 18. Thereby, the rubber membrane 18 is compressed against the pressure of the liquid column and seals the container so that no liquid can seep into the centrifuge cup 56.

In addition to the outer sealing of the container, the inner sealing is effected by the annular protrusion 43 (FIG. 2) and 45 (FIG. 5), respectively, as well as by the cooperating locking profiles 40 and 44 (FIGS. 2 and 3). Thus, liquid is prevented from entering the annular gap 12 which would prevent the expanding of the soft inner tubule 11. Due to the expanding of the inner tubule 11 during centrifugation, the plunger surface 34 of the separating member 33 no longer provides a seal. The separating member 33 takes a position between the two blood phases to be separated. After centrifugation, the inner tubule 11 will contract again and will fit in sealing manner around the plunger surface 34 of the separating member 33.

The closing cap 55 may be designed such that it may be pierced with a sampling needle. This allows taking samples in a closed system.

Alternatively to the above embodiment, the blood-taking device may contain a vacuum in order to draw blood. In this case, the inner tubule will only hold the separating member 33 and the plunger rod 35 may be dispensed with.

We claim:

1. A blood-taking device, comprising:

a radially expandable inner tubule having a front end, an outer tubule surrounding the inner tubule and having a front end, the inner tubule being relatively less rigid than the outer tubule, the inner and outer tubules mutually defining an annular gap therebetween, a separating member disposed in the inner tubule, the inner tubule and the outer tubule being clamped together at their respective front ends, whereby the inner tubule and the outer tubule are fixed with respect to each other, the front end of the inner tubule comprising an integral end wall defining a locking profile, the front end of the outer tubule comprising an integral end wall having a cone extending therefrom and defining a counter profile, the locking profile and the counter profile being mutually configured to cooperatively form a lock and seal.

2. The device of claim 1, wherein the outer tubule defines a strengthened portion having an inner surface, the locking profile comprises an outwardly directed annular protrusion on the inner tubule, and the counter profile comprises an annular depression on the inner surface of the strengthened portion of the outer tubule.

3. The device of claim 1, wherein the cone defines a channel, the end wall of the outer tubule has at least one annular protrusion surrounding the channel, the inner tubule comprises a relatively less rigid material than the outer tubule, and the annular protrusion is configured for pressing into the relatively less rigid material of the inner tubule.

4. The device of claim 1, wherein the cone defines a channel, the end wall of the inner tubule has at least one annular protrusion surrounding the channel, and the annular protrusion is configured to be flattened by the end wall of the outer tubule.

5. The device of claim 3, wherein the annular protrusion comprises a tip directed toward the end wall of the inner tubule.

6. The device of claim 1, wherein the inner tubule comprises a rear portion, the separating member comprises a plunger surface, and the rear portion of the inner tubule defines a strengthened wall portion and a circumferentially extending interior braking groove configured for receiving the plunger surface of the separating member in locking engagement.

7. The device of claim 1, comprising:

a centrifuge cup, and an insert configured to fit in the centrifuge cup, the insert comprising a pierceable membrane and a pin for supporting the membrane, the insert being adapted to center a cannula hub situated on the cone.

* * * * *